(12) United States Patent
Amyot et al.

(10) Patent No.: US 9,020,217 B2
(45) Date of Patent: Apr. 28, 2015

(54) SIMULATION OF MEDICAL IMAGING

(75) Inventors: Robert Amyot, Montreal (CA);
Sebastien Nadeau, Longueuil (CA);
Stephane Pilette, Canton de Hatley (CA); Jean-Marc Rousseau, Montreal (CA); Yanick Beaulieu, Senneville (CA)

(73) Assignee: Cae Healthcare Canada Inc., Saint-Laurent, Quebec ( * ) Notice: Subject to any disclaimer, the term of this patent is extended or adjusted under 35 U.S.C. 154(b) by 1069 days.

(21) Appl. No.: 13/120,936

(22) PCT Filed: Sep. 24, 2009

(86) PCT No.: PCT/CA2009/001351
§ 371 (c)(1),
(2), (4) Date: Sep. 15, 2011

(87) PCT Pub. No.: WO2010/034117
PCT Pub. Date: Apr. 1, 2010

(65) Prior Publication Data
US 2012/0128218 A1 May 24, 2012

Related U.S. Application Data

(60) Provisional application No. 61/100,083, filed on Sep. 25, 2008.

(51) Int. Cl.
*G06K 9/00* (2006.01)
*G06T 19/00* (2011.01)
*G09B 23/28* (2006.01)

(52) U.S. Cl.
CPC ............. *G06T 19/00* (2013.01); *G06T 2210/41* (2013.01); *G09B 23/286* (2013.01)

(58) Field of Classification Search
CPC ........... G06T 3/00; G06T 15/00; G06T 15/08; G06T 17/00; G06T 19/00; G06T 2200/04; G06T 2200/08; G06T 2207/10072; G06T 2207/10076; G06T 2207/10136; G06T 2207/20108
See application file for complete search history.

(56) References Cited

U.S. PATENT DOCUMENTS 3,674,018 A 7/1972 Goldberg
3,913,061 A 10/1975 Green
(Continued)

FOREIGN PATENT DOCUMENTS

CA 2064914 A1 3/1991
CA 2084545 6/1993
(Continued)

OTHER PUBLICATIONS

English abstract of JP 9313485.
(Continued)

*Primary Examiner* — Manav Seth
(74) *Attorney, Agent, or Firm* — BCF LLP

(57) ABSTRACT

There is described a method for simulating an imaging process for an organ, the method comprising: retrieving from a memory a 3D volume model of the organ, the 3D volume model describing a 3D structure of the organ and a distribution of density within the 3D structure, the 3D structure representing a surface and internal features of the organ; generating a slice of the 3D model according to a position and an orientation of an imaging device, the slice including a cross-section of the surface and the internal features; rendering an image in accordance with the slice; and displaying the image.

25 Claims, 14 Drawing Sheets

(56) References Cited

U.S. PATENT DOCUMENTS

| | | | |
|---|---|---|---|
| 4,265,251 A | 5/1981 | Tickner | |
| 4,729,019 A | 3/1988 | Rouvrais | |
| 4,867,167 A | 9/1989 | Magnin | |
| 4,894,013 A | 1/1990 | Smith et al. | |
| 5,050,610 A | 9/1991 | Oaks et al. | |
| 5,052,934 A | 10/1991 | Carey et al. | |
| 5,063,931 A | 11/1991 | Leavitt | |
| 5,151,856 A * | 9/1992 | Halmann et al. | 600/508 |
| 5,454,371 A * | 10/1995 | Fenster et al. | 600/443 |
| 5,462,059 A | 10/1995 | Ferrara et al. | |
| 5,609,485 A | 3/1997 | Bergman et al. | |
| 5,630,034 A | 5/1997 | Oikawa et al. | |
| 5,634,797 A | 6/1997 | Montgomery | |
| 5,724,978 A | 3/1998 | Tenhoff | |
| 5,733,259 A | 3/1998 | Valcke et al. | |
| 5,737,506 A * | 4/1998 | McKenna et al. | 345/582 |
| 5,782,762 A * | 7/1998 | Vining | 600/407 |
| 5,825,908 A * | 10/1998 | Pieper et al. | 382/131 |
| 5,842,473 A * | 12/1998 | Fenster et al. | 600/445 |
| 5,871,019 A | 2/1999 | Belohlavek | |
| 5,908,390 A | 6/1999 | Matsushima | |
| 5,964,707 A * | 10/1999 | Fenster et al. | 600/443 |
| 5,967,977 A | 10/1999 | Mullis et al. | |
| 5,971,767 A * | 10/1999 | Kaufman et al. | 434/267 |
| 6,014,473 A | 1/2000 | Hossack et al. | |
| 6,048,316 A | 4/2000 | Zhao et al. | |
| 6,080,107 A | 6/2000 | Poland | |
| 6,083,162 A * | 7/2000 | Vining | 600/407 |
| 6,120,453 A | 9/2000 | Sharp | |
| 6,151,404 A * | 11/2000 | Pieper | 382/128 |
| 6,258,339 B1 | 7/2001 | Schutt et al. | |
| 6,272,366 B1 * | 8/2001 | Vining | 600/407 |
| 6,331,116 B1 * | 12/2001 | Kaufman et al. | 434/262 |
| 6,334,847 B1 * | 1/2002 | Fenster et al. | 600/443 |
| 6,343,936 B1 * | 2/2002 | Kaufman et al. | 434/262 |
| 6,364,835 B1 | 4/2002 | Hossack et al. | |
| 6,366,800 B1 * | 4/2002 | Vining et al. | 600/425 |
| 6,544,178 B1 | 4/2003 | Grenon et al. | |
| 6,549,200 B1 | 4/2003 | Mortlock et al. | |
| 6,694,163 B1 * | 2/2004 | Vining | 600/407 |
| 6,748,347 B1 * | 6/2004 | Dalton | 703/5 |
| 6,771,262 B2 * | 8/2004 | Krishnan | 345/424 |
| 6,780,152 B2 | 8/2004 | Ustuner et al. | |
| 6,801,643 B2 * | 10/2004 | Pieper | 382/128 |
| 6,828,973 B2 * | 12/2004 | Fery | 345/473 |
| 7,012,603 B2 * | 3/2006 | Chen et al. | 345/419 |
| 7,043,292 B2 | 5/2006 | Tarjan et al. | |
| 7,066,887 B2 | 6/2006 | Flesch et al. | |
| 7,102,634 B2 * | 9/2006 | Kim et al. | 345/419 |
| 7,109,557 B2 | 9/2006 | Barns et al. | |
| 7,149,333 B2 * | 12/2006 | Pieper et al. | 382/128 |
| 7,194,117 B2 * | 3/2007 | Kaufman et al. | 382/128 |
| 7,194,919 B2 | 3/2007 | Shkarlet et al. | |
| 7,197,170 B2 * | 3/2007 | Dwyer et al. | 382/128 |
| 7,329,225 B2 | 2/2008 | Smith et al. | |
| 7,416,554 B2 | 8/2008 | Lam et al. | |
| 7,702,137 B2 * | 4/2010 | Dwyer et al. | 382/128 |
| 7,704,264 B2 | 4/2010 | Ewers et al. | |
| 7,805,177 B2 * | 9/2010 | Chen et al. | 600/407 |
| 7,835,892 B2 | 11/2010 | Butsev et al. | |
| 7,877,149 B2 | 1/2011 | Zdeblick | |
| 7,912,528 B2 | 3/2011 | Krishnan et al. | |
| 2002/0088926 A1 | 7/2002 | Prasser | |
| 2003/0045803 A1 | 3/2003 | Acharya | |
| 2004/0162568 A1 | 8/2004 | Saadat et al. | |
| 2004/0225183 A1 | 11/2004 | Michlitsch et al. | |
| 2005/0043609 A1 | 2/2005 | Murphy et al. | |
| 2007/0161894 A1 | 7/2007 | Zdeblick et al. | |
| 2007/0168339 A1 | 7/2007 | Vezina et al. | |
| 2007/0191871 A1 | 8/2007 | Baker et al. | |
| 2008/0186378 A1 | 8/2008 | Shen et al. | |

FOREIGN PATENT DOCUMENTS

| | | |
|---|---|---|
| CA | 2227543 A1 | 2/1997 |
| CA | 2236958 A1 | 11/1998 |
| CA | 2521719 A1 | 11/2004 |
| CA | 2530419 A1 | 1/2005 |
| CA | 2582519 A1 | 4/2006 |
| CA | 2554274 A1 | 2/2007 |
| CA | 2554304 A1 | 2/2007 |
| CA | 2554311 A1 | 2/2007 |
| CN | 1230271 A | 9/1999 |
| CN | 1266725 A | 9/2000 |
| EP | 0931508 A1 | 7/1999 |
| EP | 0961135 A1 | 12/1999 |
| EP | 1321101 A2 | 6/2003 |
| EP | 1057453 B1 | 6/2004 |
| EP | 1508872 A1 | 2/2005 |
| FR | 2623317 A1 | 5/1989 |
| FR | 2755020 A1 | 4/1998 |
| JP | 55054942 A | 4/1980 |
| JP | 7055775 A2 | 3/1995 |
| JP | 9313485 A | 12/1997 |
| JP | 2000300551 A | 10/2000 |
| JP | 2003282346 A | 10/2003 |
| JP | 2006026079 A | 2/2006 |
| LT | 4831 B | 8/2001 |
| NO | 982447 A | 11/1998 |
| RU | 2147382 C1 | 4/2000 |
| RU | 2147835 C1 | 4/2000 |
| WO | 9310711 A1 | 6/1993 |
| WO | 9634375 A1 | 10/1996 |
| WO | 9811524 A1 | 3/1998 |
| WO | 9951300 A2 | 10/1999 |
| WO | 9955233 A1 | 11/1999 |
| WO | 0015107 A1 | 3/2000 |
| WO | 0126557 A1 | 4/2001 |
| WO | 0189359 A2 | 11/2001 |
| WO | 02054379 A2 | 7/2002 |
| WO | 02094080 A2 | 11/2002 |
| WO | 02095653 A2 | 11/2002 |
| WO | 03077766 A1 | 9/2003 |
| WO | 2004070553 A2 | 8/2004 |
| WO | 2005007075 A2 | 1/2005 |
| WO | 2005030089 A2 | 4/2005 |
| WO | 2005058239 A2 | 6/2005 |
| WO | 2005070061 A2 | 8/2005 |
| WO | 2005077293 A2 | 8/2005 |
| WO | 2006029037 A2 | 3/2006 |
| WO | 2006042039 A2 | 4/2006 |
| WO | 2006044996 A2 | 4/2006 |
| WO | 2006050385 A2 | 5/2006 |
| WO | 2006068271 A1 | 6/2006 |
| WO | 2006104959 A2 | 10/2006 |
| WO | 2007067323 A2 | 6/2007 |
| WO | 2007074668 A1 | 7/2007 |
| WO | 2007097247 A1 | 8/2007 |

OTHER PUBLICATIONS

English abstract of LT 4831.
English abstract of JP 2006026079.
English abstract of JP 2000300551.
English abstract of NO 982447.
English abstract of JP 7055775.
English abstract of JP 2003282346.
English abstract of RU 2147382.
English abstract of RU 2147835.
English abstract of FR 2623317.
English abstract of FR 2755020.
English abstract of EP 0931508.
English abstract of EP 1321101.
International Search Report of PCT/CA2009/001351; Dec. 16, 2009; Goran Basic.
English abstract of CN123271 retrieved from Espacenet on May 7, 2013.

* cited by examiner

SIMULATION OF MEDICAL IMAGING

CROSS-REFERENCE TO RELATED APPLICATIONS

The present application is a United States National Stage Entry of International Application Number PCT/CA2009/001351, filed on Sep. 24, 2009, and claims priority to U.S. Provisional Patent Application No. 61/100,083, filed on Sep. 25, 2008, the entirety of both of which is incorporated herein by reference.

TECHNICAL FIELD

The present invention relates to the field of simulation of medical imaging, and particularly to medical imaging using imaging devices, such as probes for ultrasound imaging.

BACKGROUND

Ultrasound imaging simulators are used to train students to the technique of ultrasonography. However, the training offered using these types of devices is limited. Certain ultrasonographic diagnosis training apparatuses use 3-D arrays of ultrasonographic datasets based on the precise scanning of a real person's body with an ultrasound device or other medical diagnosis apparatuses, which is time-consuming and costly to obtain. The various ultrasonographic "slices" obtained during scanning are then saved in a database, and interpolation techniques are used to fill the gaps between slices. Most of the time the datasets are from healthy patients, or from patients with minor pathologies that do not require immediate treatment. It is very difficult to obtain ultrasonographic datasets with rare pathologies or disease conditions that require immediate intervention, as those patients are often not available for a prolonged time to do a complete scan of the region of interest or organ.

Furthermore, there is a finite amount of data in each case or dataset. The scanning windows and angles are limited in comparison to a real, clinical examination. The instructor and student may find themselves striving for an even better image, but that perfect image is often beyond the capabilities of the stored data.

Therefore, there is a need for improving ultrasonographic diagnosis training devices.

SUMMARY

The method proposed herein involves the generation of a 3D model of an organ using volume modeling. Unlike wire frame and surface modeling, volume modeling systems ensure that all surfaces meet properly and that the object is geometrically correct. Volume modeling simulates an object internally and externally. Volumic 3D models can be sectioned to reveal their internal features. When an object is built as a 3D model, cross sections of its internal structure can be rendered as if it were sliced.

The virtual 3-D model generated using volume modeling can be animated, to reproduce a beating heart for example, and therefore this technique may be used to image dynamic organs as well as static ones. In addition, the method covers non-invasive, semi-invasive, and invasive ultrasonography simulation techniques. Transthoracic echocardiography, transesophageal echocardiography, and intracardiac echography are examples of non-invasive, semi-invasive, and invasive ultrasound imaging techniques, respectively.

In accordance with a first broad aspect, there is provided a method for simulating an imaging process for an organ, the method comprising: retrieving from a memory a 3D volume model of the organ, the 3D volume model describing a 3D structure of the organ and a distribution of density within the 3D structure, the 3D structure representing a surface and internal features of the organ; generating a slice of the 3D model according to a position and an orientation of an imaging device, the slice including a cross-section of the surface and the internal features; rendering an image in accordance with the slice; and displaying the image.

In accordance with a second broad aspect, there is provided a computer readable memory having recorded thereon a set of data representative of a 3D volume model of an organ and statements and instructions for execution by a processor to carry out steps of slicing the 3D volume model in accordance with a position and orientation of an imaging device, rendering an image in accordance with the slice, and displaying the image, the 3D volume model describing a 3D structure of the organ and a distribution of density within the 3D structure, the 3D structure representing a surface and internal features of the organ, the slice including a cross-section of the surface and the internal features.

In accordance with a further broad aspect, there is provided a system for simulating an imaging process, comprising: an imaging device; a position tracking device adapted to determine a position and orientation of the imaging device; and a machine comprising a memory having a set of data representative of a 3D volume model of an organ stored therein and a processor configured for slicing the 3D volume model in accordance with the position and orientation of the imaging device, rendering an image in accordance with the slice, and displaying the image on a display unit, the 3D volume model describing a 3D structure of the organ and a distribution of density within the 3D structure, the 3D structure representing a surface and internal features of the organ, the slice including a cross-section of the surface and the internal features.

It should be understood that the terms "echography", "ultrasonography", and "medical sonography" can interchangeably be used.

The term "organ" should be understood as any element or structure of a living being that can be scanned by ultrasound, including muscles, tendons and internal organs such as a heart, liver and the like. A foetus is also another example of an organ.

BRIEF DESCRIPTION OF THE DRAWINGS

Further features and advantages of the present invention will become apparent from the following detailed description, taken in combination with the appended drawings, in which.

DETAILED DESCRIPTION

Figure 1A:
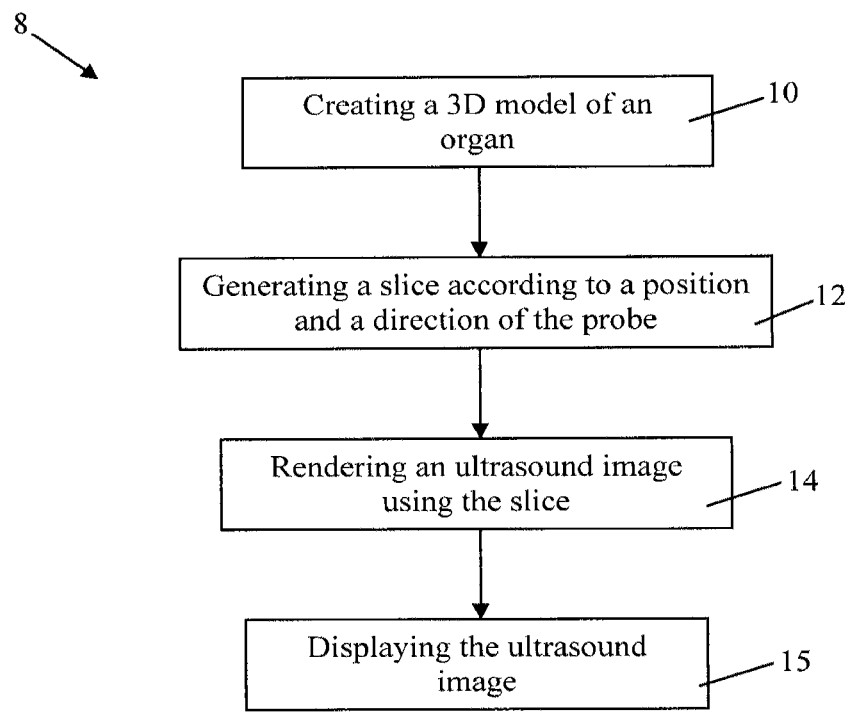
FIG. 1a is a flow chart of a method for simulating an ultrasound image of an organ, in accordance with an embodiment.

FIG. 1a illustrates one embodiment of a method 8 for simulating an ultrasound image of an organ. The first step 10 of the method 8 consists in the creation of a 3D volume model of the organ. The 3D model which may be stored in a memory comprises a 3D structure of the organ which includes both a 3D surface and the internal features of the organ. The 3D surface of the organ comprises the external surface of the organ and may also comprise internal surfaces. Data such as density is distributed within the 3D model. The internal features comprise elements contained within the external surface of the organ, such as muscle myocytes, veins, arteries, cavities, and the like. Taking the example of a heart, the 3D model takes into account internal features such as the endocardium, ventricular cavities, papillary muscles, valves, and the like. Furthermore, the 3D model may also be modified to include any pathology, even rare pathologies.

Figure 1B:
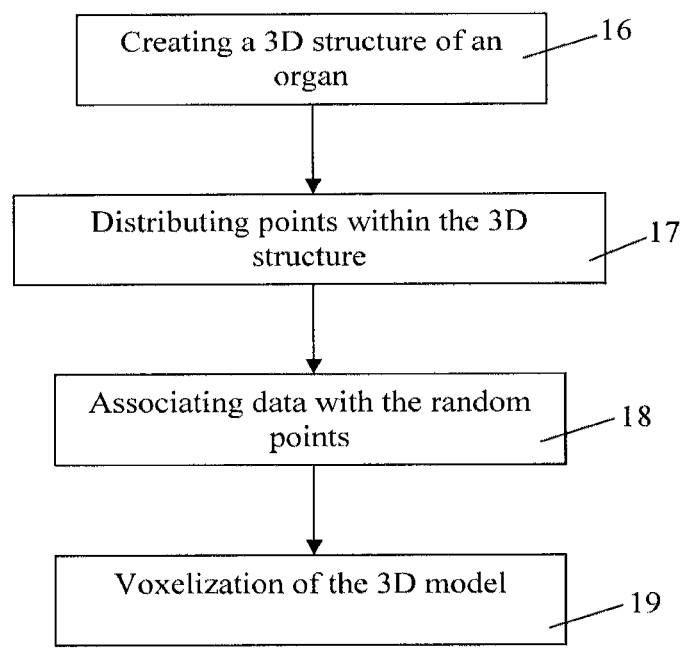
FIG. 1b is a flow chart of a method for creating a 3D model in accordance with an embodiment.
Figure 2:
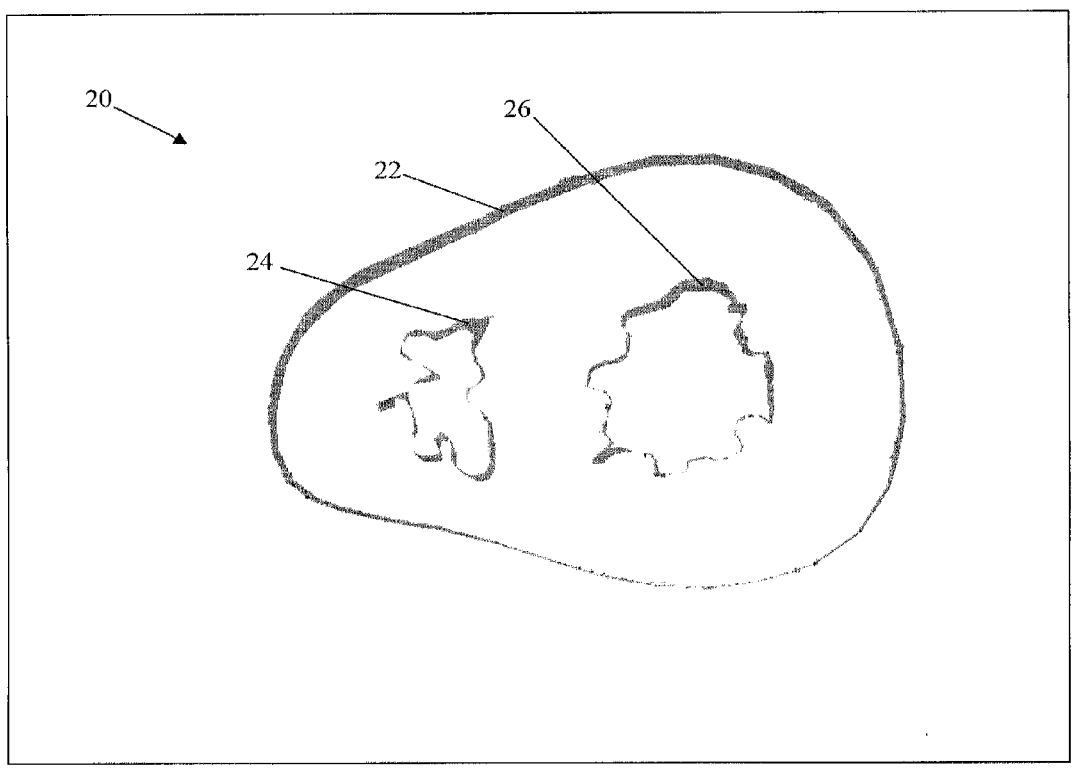
FIG. 2 is cross-section of a 3D structure of a heart, in accordance with an embodiment.

In one embodiment, the creation of the 3D model 10 comprises four steps, as illustrated in FIG. 1b. The first step 16 is the generation of a 3D structure of the organ. The 3D structure is an empty model of the organ representing the external outline of the organ. The empty model comprises the external surface of the organ. In other words, the first step 16 is the creation of the external envelop of the organ. The 3D structure may also comprise internal features of the organ. In this case, the empty model also comprises the surface of any internal features. Taking the example of a heart, FIG. 2 illustrates a cross-section 20 of an empty model of a heart. The empty model of the heart comprises the external surface 22 of the heart and the surface of internal cavities 24 and 26. It should be understood that the surface of the internal cavities 24 and 26 may be omitted in the 3D structure. Any surface modeling technique such as polygonal surface modeling or non-uniform rational B-spline modeling can be used to generate the empty model.

Figure 3:
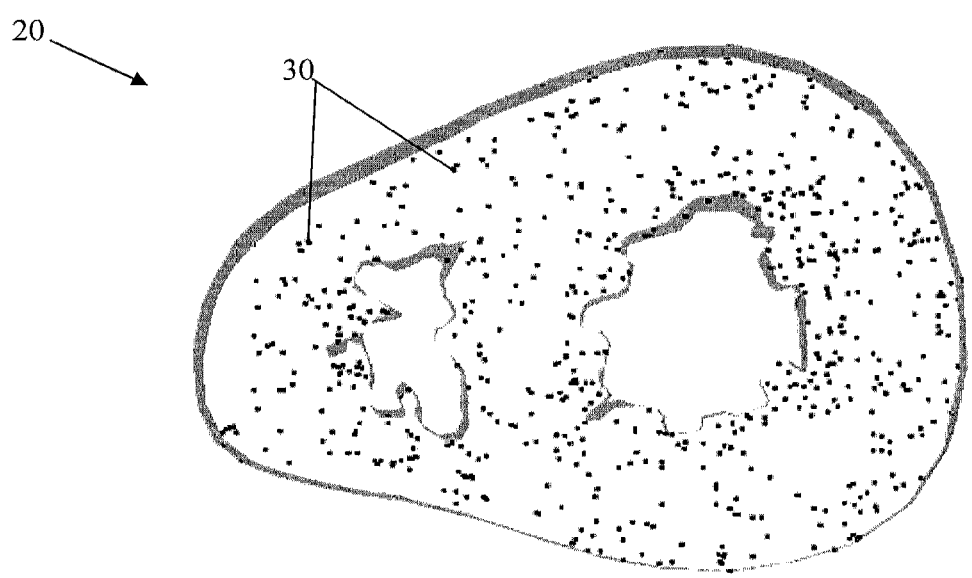
FIG. 3 is a cross-section of a 3D structure of a heart filled with random points, in accordance with an embodiment.

The second step 17 of the creation of the 3D model 10 is a distribution of points within the 3D structure of the organ. In one embodiment, the points are randomly distributed within the 3D structure of the organ. FIG. 3 illustrates the cross-section of the heart 20 in which points 30 have been randomly distributed. Alternatively, the points 30 may be spatially organized in accordance with a predetermined spatial pattern. For example, points 30 may be aligned along predetermined lines and successive points 30 may be spaced apart by a predetermined distance. While in FIG. 3 no points 30 are present in the cavities 24 and 26, it should be understood that some points 30 may be distributed within the cavities 24 and 26.

The next step 18 is the association of data with each point 30. Data such as a value of density is associated with each point 30. In FIG. 3, the regions comprising no points 30 are considered as being regions having a zero density and appear as black on the simulated ultrasound image. If points 30 are present in the cavities 24 and 26, the density value associated with these points is set to zero.

In one embodiment where the organ comprises internal features, the 3D structure of the organ generated at step 16 comprises no internal features. In this case, at step 17, points 30 are distributed within the 3D structure in a random or organized way, and at step 18, data such as a density value is associated with each point 30. The internal features of the organ are generated in the 3D model by setting the value of data associated with some points to a particular value. For example, the value of the density of points 30 contained in the regions of the 3D structure corresponding to the cavities 24 and 26 may be set to zero. These particular zero density regions appear as black on the simulated ultrasound image.

In one embodiment, an influence parameter R is also associated with each point 30. The parameter R can be a radius defining a sphere centered on the point 30. The density value of any point within the sphere is defined by the density value associated with the center of the sphere, namely point 30. It should be understood that the parameter R may be used to define a 3D object different from a sphere. For example, the parameter R may define a cube centered on the point 30 and the density value of any point within the cube is defined by the density value associated with the center of the cube, namely point 30. In one embodiment, the parameter R may be fixed for all of the points 30 throughout the 3D model. Alternatively, the parameter R may vary from one point 30 to another. For example, large spheres may be used in regions of the organ where the density varies progressively whereas small spheres are used in regions where the density varies widely within small regions.

Figure 4:
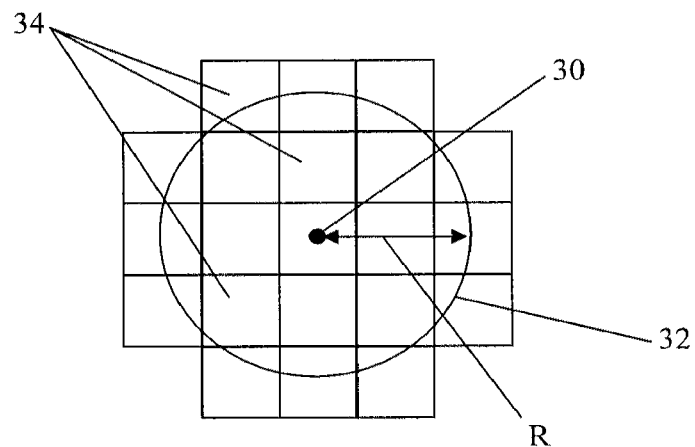
FIG. 4 illustrates the voxelization of a sphere associated with a random point, in accordance with an embodiment.

The fourth step 19 of the generation of the 3D model 10 is the voxelization of the model. The 3D model comprising the points 30 is divided into a plurality of unitary volume elements (voxels). A volume value, an index indicative of a 3D spatial position, and a density value are associated with each voxel. The density value associated with each voxel is defined as a function of the density value of the point 30 to which it is related. FIG. 4 illustrates the voxelization associated with a point 30.

In one embodiment, a density value d1 and a radius R are associated with each point 30. The point 30 is the center of a sphere 32 having a radius R. The voxelization generates voxels 34 which intersect the sphere 32. The sphere 32 defines an area of influence of the center of the sphere 30 for the assignment of density values to voxels. A value of density is attributed to each voxel 34 as a function of the density value d1 associated with the point 30.

In one embodiment, each voxel 34 shares the same density value d1 as that associated with the point 30. Alternatively, the density value associated with a particular voxel 34 may depend on the density value of the point 30 and the distance between the particular voxel and the point 30. The density value associated with a particular voxel 34 may also depend on more than one point 30 surrounding the voxel 34.

In the case of a voxel 34 belonging to more than one sphere 32, its density may be an average of the density values of the centers of the spheres to which it belongs. In the case of a voxel comprising two points 30, a sub-sampling can be performed. This means that voxels of smaller sizes are generated so that each point 30 is comprised in a different voxel. It should be understood that any mathematical method to assign a density value to voxels as a function of the density value of points 30 may be used.

In one embodiment, the voxelization step 19 is omitted and an ultrasound image is generated directly from the cloud of points 30 and their associated data, such as a density value. A parameter R, defining a sphere for example, may also be associated with each point 30 of the cloud. In this case, the density value of the points contained in the sphere is determined in accordance with the density value of the center of the sphere, namely point 30. The use of the parameter R allows for the reduction of the number of points 30 required to create the 3D model of the organ.

Animated 3D models can also be created. For example, images of a beating heart may be simulated. Another example is a live foetus. Any movement and/or any frequency of the movement can be included in the 3D model. In one embodiment, in order to animate the 3D model, at least one of the density, the radius and the position associated with points 30 is varied in time. Furthermore, the 3D structure may also be animated so that the shape of the organ including its internal features may vary in time. It should be understood that any animation technique for animating the organ, such as object deformation techniques, may be used.

In another embodiment, solid modeling is used to create the 3D model of the organ. In this case, the 3D model of the organ is directly achieved by a 3D assembly of voxels. Data such as a density value is associated with each one of the voxels. The value of density varying from one voxel to another allows the internal features of an organ to be defined. The size of the voxels may be constant throughout the modeled heart. Alternatively, the size of the voxels may vary within the model. The size of the voxels may depend on the variation rate of the density within the organ. For example, large voxels may be used in regions of the organ where the density varies progressively whereas small voxels are used in regions where the density varies widely within small regions.

Animated solid 3D models can also be created. In one embodiment, the organ is represented by a dataset of dynamic voxels or doxels. A doxel is a voxel with another dimension, namely time. Each doxel is a matrix in which a value of density is associated with each time t. It should be understood that each doxel can also contain information on properties other than density. Any technique known by a person skilled in the art to make an animated 3D model of an organ can be used.

Any technique known by a person skilled in the art to create a 3D model of an organ comprising at least a density value associated with points of the model can be used. It should be noted that values of various properties can be associated with each point or voxel of the model. Any method known by a person skilled in the art to animate a 3D model can be used.

In one embodiment, the step of distributing points comprises distributing points 30 outside of the 3D structure of the organ in order to take into account elements surrounding the organ, such as bones or other organs for example. In this case, the step 18 of associating data with points comprises associating data with the external points located outside the 3D structure of the organ. Data such as density is associated with these external points and a parameter R may also be associated with each one of these external points in order to generate spheres, cubes or the like. When a voxelization step 19 is present, this step comprises the voxelization of the region surrounding the organ in which external points have been distributed. In one embodiment in which solid modeling is used to generate the 3D model of the organ, voxels or doxels can be distributed outside of the 3D structure of the organ, and data such as density is associated with the voxels or doxels external to the organ in order to represent the surroundings of the organ.

Figure 5:
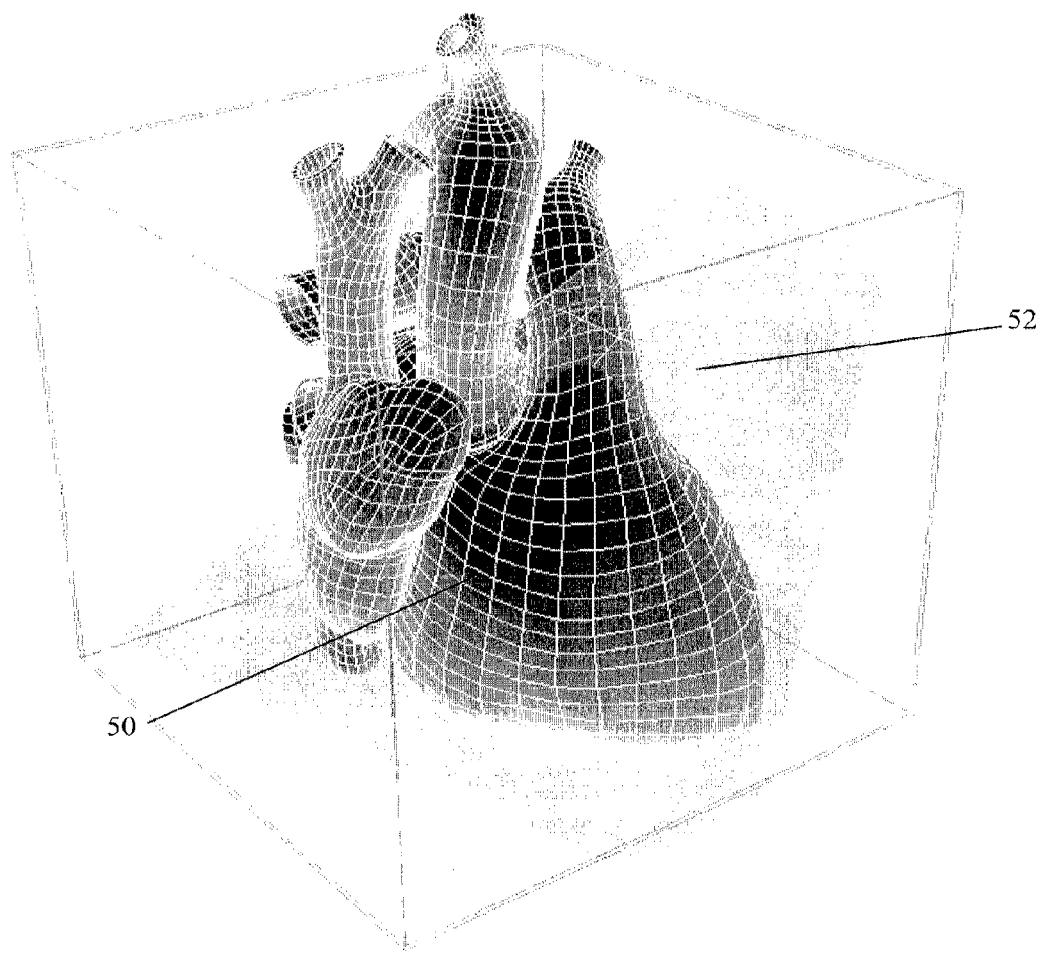
FIG. 5 illustrates a 3D heart intersected by a first cross-sectional plane, in accordance with an embodiment.

Referring back to FIG. 1*a*, step 12 of the method comprises the generation of a planar slice of the 3D model. The slice is generated according to a position and an orientation of a probe and has a given thickness. The thickness of the slice is chosen so that the simulated ultrasound image realistically reproduces a real ultrasound image. The position and orientation of the probe define a cross-sectional plane 52, as illustrated in FIG. 5. The slice is defined according to the cross-sectional plane. The next step 14 comprises the rendering of an ultrasound image using the slice generated at step 12. The volumes resulting from the voxelization and the density values associated with each voxel provide a virtual ultrasonographic texture to the ultrasound image. The resulting ultrasound image may be colored or greyscaled. The color or grey value of each pixel of the displayed image is defined by the density value associated with its corresponding voxel. If the thickness of the slice is large enough to comprise several voxels, each pixel of the displayed image is associated with several voxels. In this case, the density value and the color associated with this pixel is a function of the density values of all of the voxels to which this pixel is associated. For example, an average density value may be calculated and used to assign a color to the particular pixel of the displayed image. The last step 15 of the method 8 illustrated in FIG. 1*a* is the displaying of the rendered ultrasound image.

While the present description refers to an embodiment in which the whole 3D model of the organ is voxelized and subsequently sliced, it should be understood that the voxelization step may be performed after slicing the model. In this case, a slice is first generated in accordance with the position and orientation of the probe and subsequently voxelized. The ultrasound image is then rendered using the voxelized slice.

In one embodiment where the voxelization step 19 is omitted, the slice comprises some points 30 each having at least one associated density value. The color or grey value of each pixel of the displayed image is defined by the density value associated with its corresponding point 30. Interpolation techniques may be used for determining the color or grey value of the pixels. If the thickness of the slice is large enough to comprise several points 30, each pixel of the displayed image is associated with several points 30. In this case, the density value and the color associated with this pixel is a function of the density values of all of the points 30 to which this pixel is associated. For example, an average density value may be calculated and used to assign a color to the particular pixel of the displayed image. If a parameter R, defining a sphere for example, is associated with each point 30, the density value and the color associated with a particular pixel is a function of the density values of all of the spheres to which the particular pixel is associated.

In one embodiment where the step of voxelization 19 is omitted, the position of points 30 can be interpolated in time to lower or increase the speed of the animation while not substantially affecting the fluidity of the motion of the displayed image. Furthermore, the cloud of points 30 may be dynamically modified or deformed in substantially real-time, thereby providing the capability to simulate a dynamic change in the shape of the simulated organ or any procedures that would affect the shape of the simulated organ such as surgical cuts.

Figure 6:
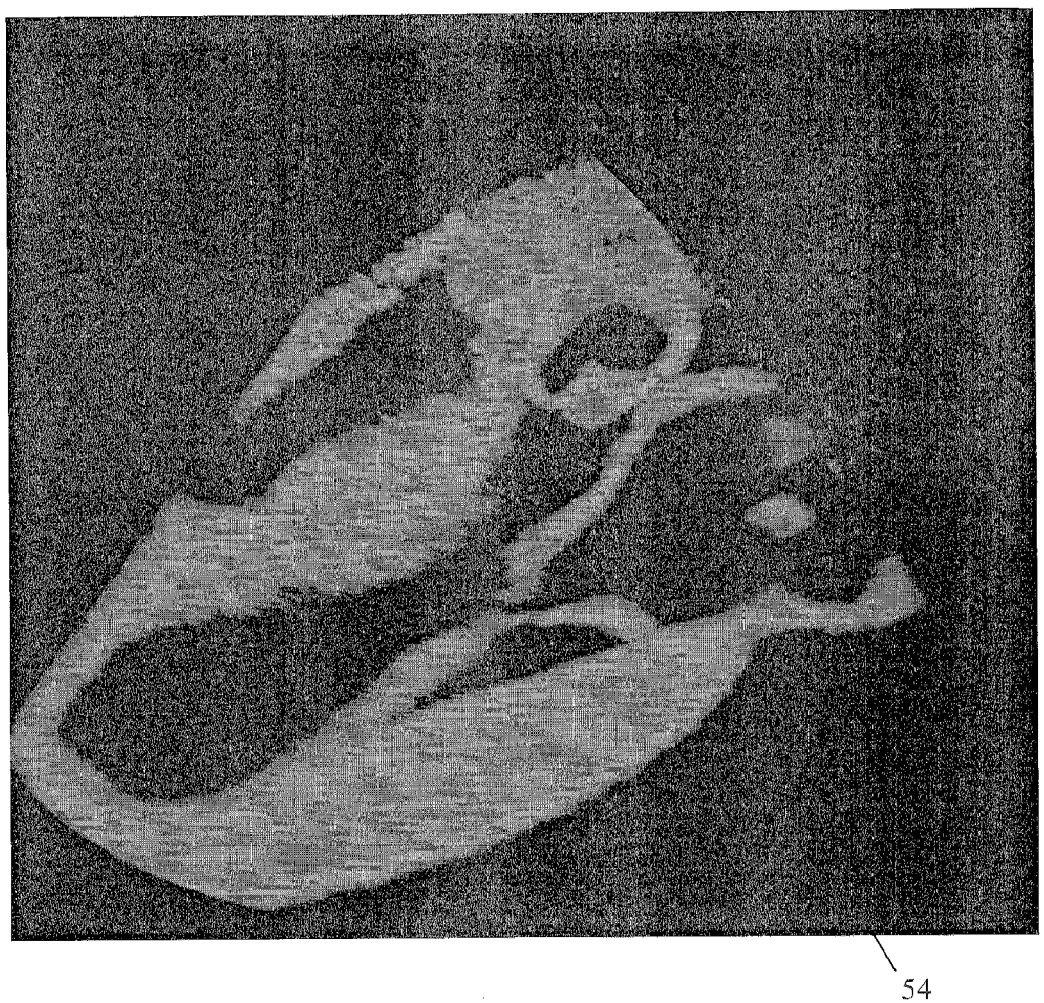
FIG. 6 illustrates a simulated ultrasound image generated according to the cross-sectional plane of FIG. 5, in accordance with an embodiment.
Figure 7:
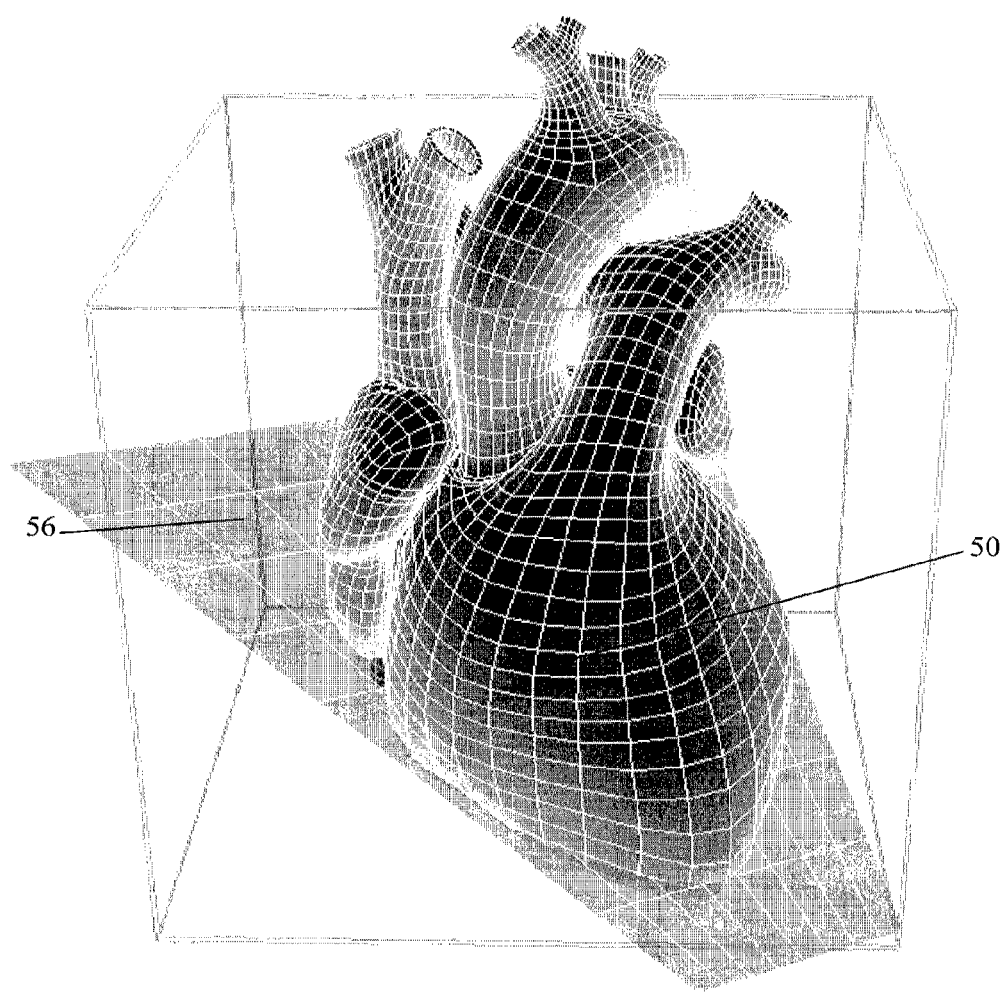
FIG. 7 illustrates the 3D heart of FIG. 5 intersected by a second cross-sectional plane, in accordance with an embodiment.
Figure 8:
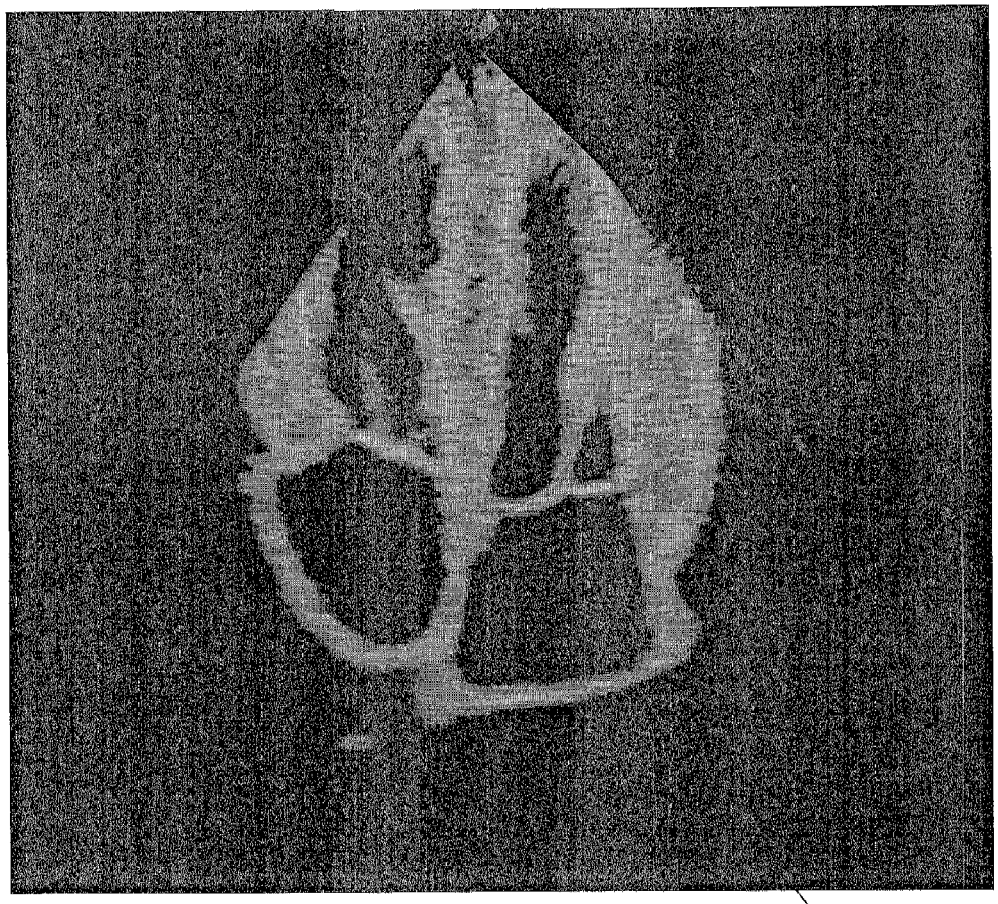
FIG. 8 illustrates a simulated ultrasound image generated according to the cross-sectional plane of FIG. 7, in accordance with an embodiment.
Figure 9:
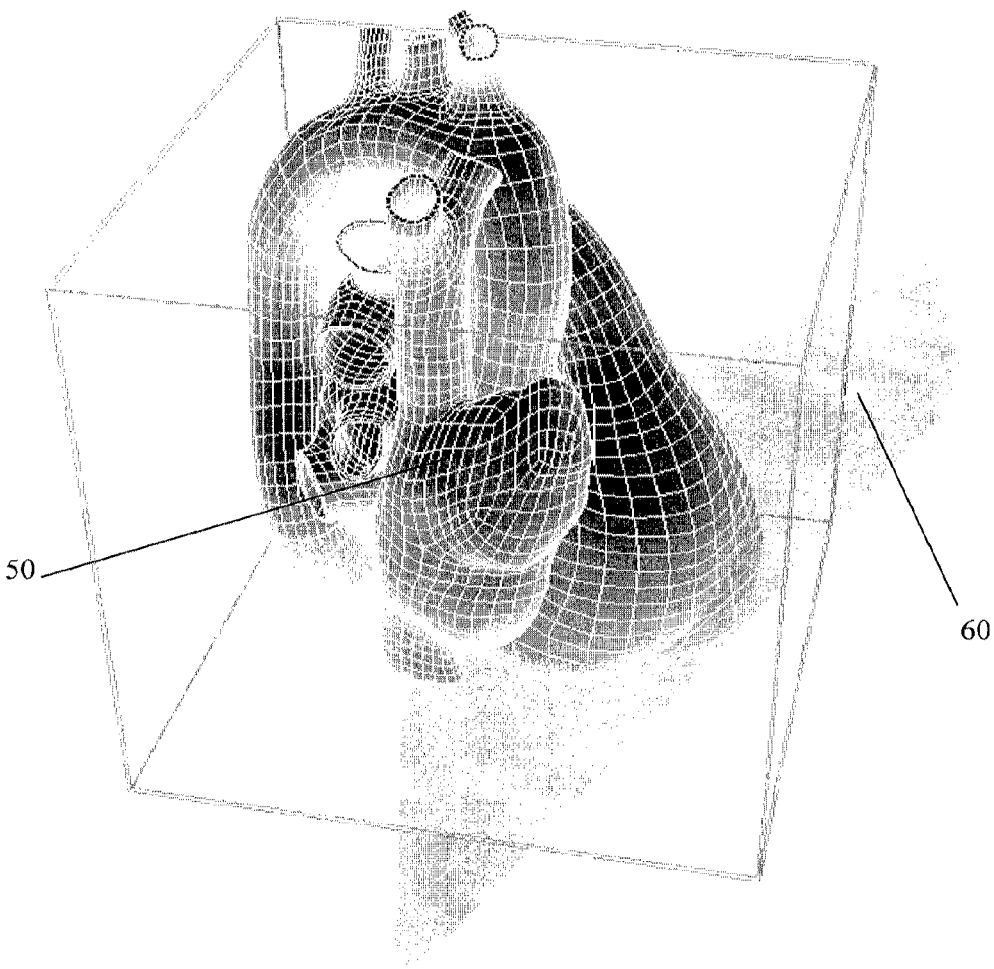
FIG. 9 illustrates the 3D heart of FIG. 5 intersected by a third cross-sectional plane, in accordance with an embodiment.
Figure 10:
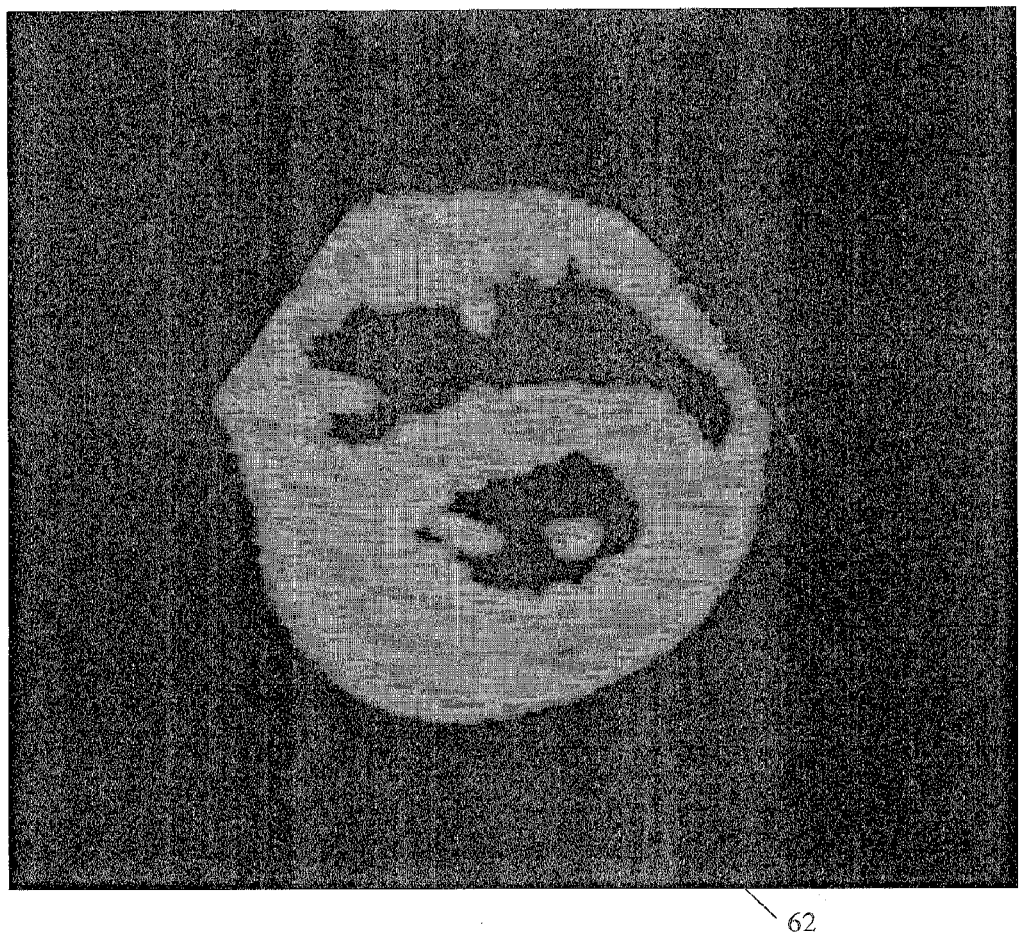
FIG. 10 illustrates a simulated ultrasound image generated according to the cross-sectional plane of FIG. 9, in accordance with an embodiment.

By varying the location and orientation of the probe, the cross-sectional plane changes and a different ultrasound image is created and displayed. FIG. 5 illustrates a 3D model of a heart 50 and a first cross-sectional plane 52 according to which the ultrasound image 54 is generated, as illustrated in FIG. 6. FIG. 7 illustrates a second cross-sectional plane 56 which corresponds to a second position and orientation of the probe. The intersection of the cross-sectional plane 56 with the 3D heart 50 generates a second ultrasound image 58, as illustrated in FIG. 8. Finally, by moving the probe to a third position and orientation, a cross-sectional plane 60 is generated, as illustrated in FIG. 9. The plane 60 intersects the modeled 3D heart 50 and a third ultrasound image 62 of the heart 50 is generated and displayed, as illustrated in FIG. 10.

Figure 11:
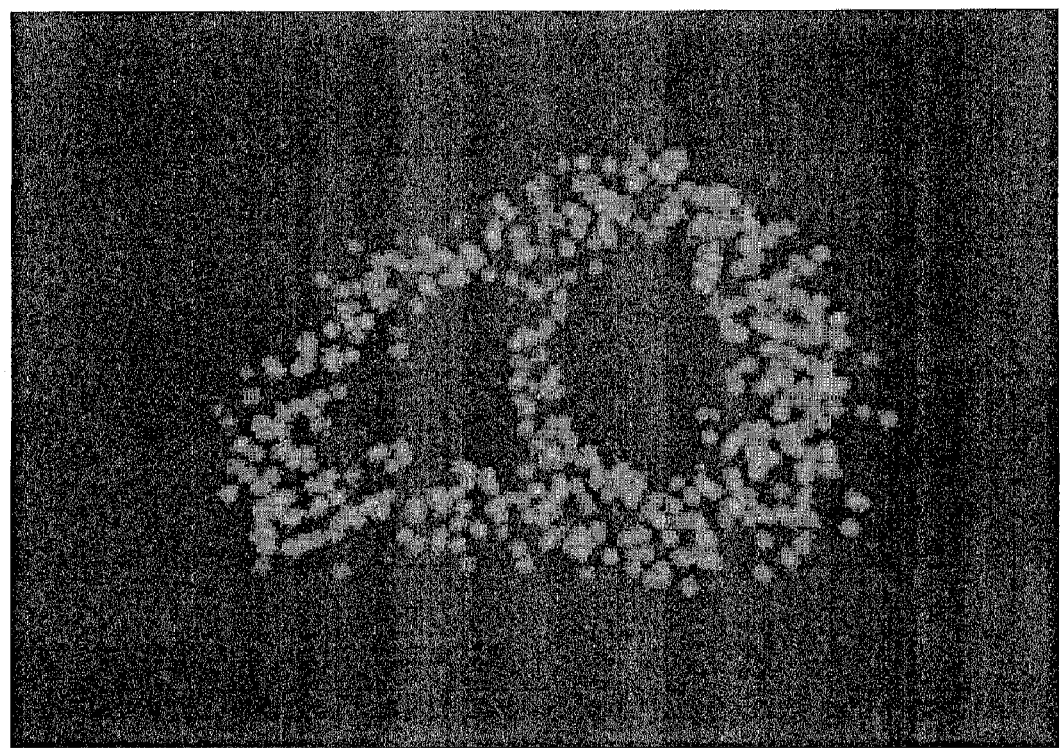
FIG. 11 illustrates a simulated ultrasound image generated from a 3D heart model before a filtering process, in accordance with an embodiment.
Figure 12:
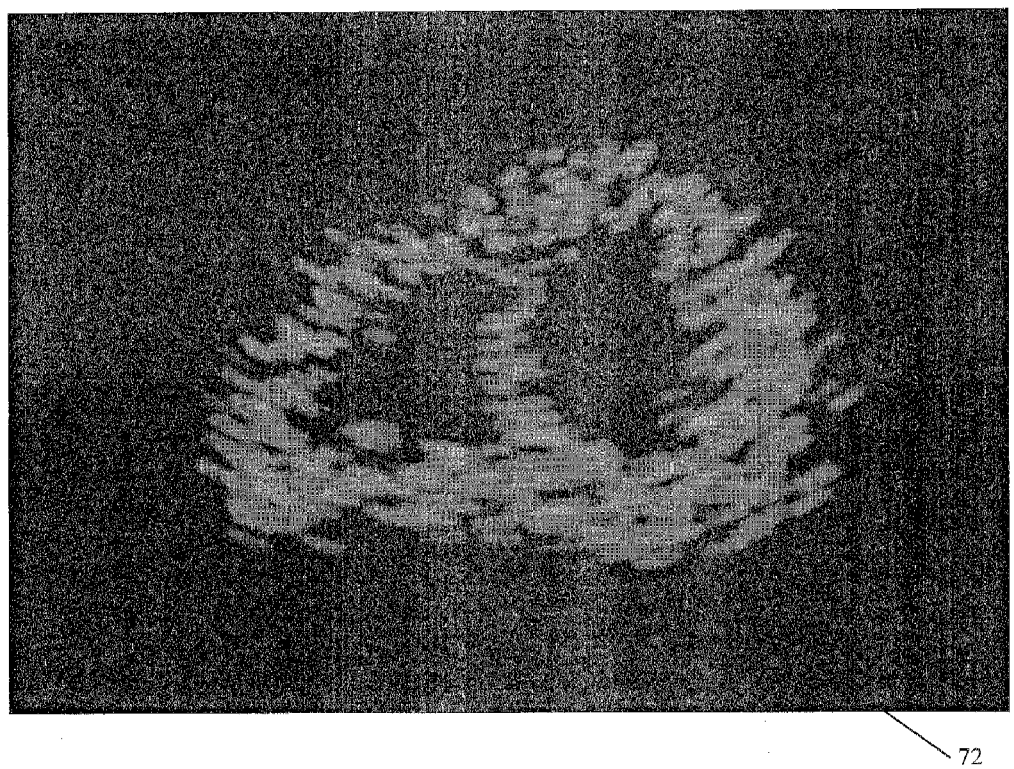
FIG. 12 illustrates a simulated ultrasound image of FIG. 11 after a filtering process, in accordance with an embodiment.

In one embodiment, the method illustrated in FIG. 1a may further comprise a step of refinement of the realistic virtual ultrasonographic texture of the image to produce a realistic ultrasonographic texture. The resulting image corresponds to a view that one would see when using a real ultrasound device. FIG. 11 illustrates a simulated ultrasonographic image 70 when no refinement of ultrasonographic texture has been performed. The refinement of the ultrasonographic texture can be performed by applying a filter to the slice. FIG. 12 illustrates an ultrasound image 72 presenting a realistic ultrasonographic texture. The ultrasound images 70 and 72 result from the same slice but a filtering step has been used to create the image 72, which results in a realistic ultrasound image.

In some instances, the creation of the ultrasonographic image may involve deteriorating the quality of the image so as to more realistically reproduce an ultrasound image. For example, the deterioration of the image may be performed in order to take into account artefacts and obstacles such as bones or other organs. The deterioration of the image may be performed in accordance with the position and orientation of the probe. Alternatively, the deterioration of the image is independent of the position and orientation of the probe.

In one embodiment, the creation of ultrasound images and their displaying is done in substantially real-time, and the displayed image substantially corresponds to the slice generated according to the actual position and orientation of the probe.

In the case of the simulation of a beating heart, the 3D model also contains time. The rendering of each image is performed according to the density values associated with each point 30 or voxel for a specific time. The animation is achieved by successively displaying the ultrasound images. For example, it is possible to simulate a beating heart of which the beating frequency varies during the ultrasound imaging simulation and likewise simulate any type of arrhythmia.

The method described above can be embodied in a machine connectable to a probe and a display, and comprising a processing unit and a memory. The 3D model of the organ is stored in the memory and the processing unit is adapted to generate a slice of the 3D model in accordance with the position and orientation of the probe, render an ultrasound image, and display the ultrasound image on the display. It should also be understood that the method described above can be embodied in a computer readable memory having recorded thereon a 3D model of an organ and statements and instructions for execution by a processor to carry out the method of slicing the 3D model in accordance with a position and orientation of a probe, rendering an ultrasound image using the slice, and displaying the ultrasound image.

Figure 13:
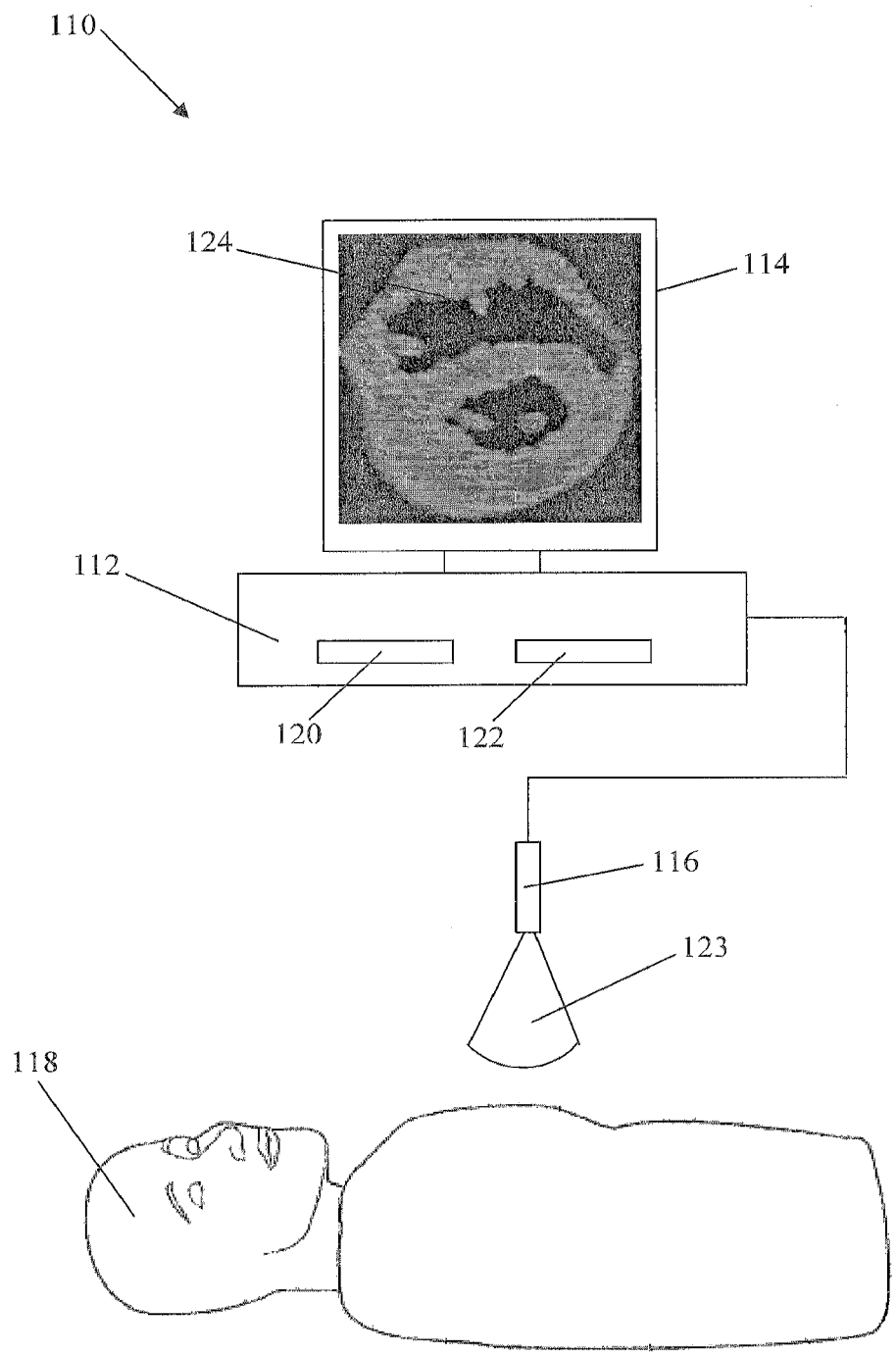
FIG. 13 illustrates an ultrasound simulator, in accordance with an embodiment.

FIG. 13 illustrates one embodiment of an ultrasound simulator 110. The ultrasound simulator 110 comprises a computer 112 connected to a monitor 114, a probe 116, and a mannequin 118. The mannequin 118 plays the role of a patient that a user to be trained has to scan via ultrasound. By displacing and orienting the probe 116, the user selects the view of the organ to be displayed.

The computer 112 comprises a memory 120 accessible by a processor 122. A 3D model of the organ comprising a 3D structure of the organ and the internal features of the organ is saved on the memory 120. In one embodiment, a data set representative of the 3D model is stored in memory 120 and comprises a cloud of position points each associated with a 3D spatial coordinate and data such as density. The position points with their associated data represent a cloud of data points distributed within the 3D structure. In one embodiment, the processor 122 is adapted to perform a voxelization of the cloud of data points in order to obtain a 3D grid of voxels or doxels. The density value of the voxels or doxels is determined as a function of the density value of the data points. Alternatively, the data set representative of the 3D model and stored in memory 120 comprises the voxels or doxels and their associated data.

The processor 122 is adapted to generate a slice of the 3D model according to a cross-sectional plane 123 defined by the position and orientation of the probe 116, and to render an ultrasound image by using the slice. In one embodiment in which the 3D model stored in memory 120 comprises the surface model of the organ and the cloud of points to which a density value is associated, the processor 122 is adapted to render the ultrasound image using the cloud of points. The ultrasound image is generated by assigning a color or a grey scale value to each point of the slice in accordance with the density values of the points of the cloud. The resulting ultrasound image 124 is displayed on the monitor 114. Alternatively, the processor 122 is adapted to perform a voxelization of the slice, calculate a density value for each voxel, and render the ultrasound image using the voxelized model. The ultrasound image is generated by assigning a color or a grey scale value to each point of the slice in accordance with the density values of the voxels associated with the particular point. In another embodiment in which the 3D model stored in memory 120 comprises voxels and associated data, the processor 122 is adapted to slice the 3D model and render an ultrasound image by assigning a color or a grey scale value to each point of the slice in accordance with the density values of the voxels associated with the particular point. The resulting ultrasound image 124 is displayed on the monitor 114.

In one embodiment of the ultrasound simulator 110, the processor 122 is adapted to refine the ultrasound texture by applying a filter to the slice.

The processor 122 generates and displays the ultrasound images 124 in substantially real-time. As a result, when the probe 116 is moved by the user, the simulator 110 displays the corresponding ultrasound image on the monitor 114 without any substantial time delay. Displacing the probe 116 results in displaying a different view of the organ.

In one embodiment of the simulator 110, the processor 122 is adapted to take into account artefacts and obstacles when rendering the ultrasound image 124. For example, the resulting ultrasound image 124 may be deteriorated in order to take into account bones or other organs located between the organ to be scanned and the probe. These artefacts and obstacles may be selected by a professor in charge of the training.

In another embodiment, the processor 122 is adapted to receive information from a position tracking system or device to determine the position and orientation of the probe 116. It should be understood that any adequate position tracking system or device may be used. For example, the position tracking system may comprise a signal emitting device and a signal receiving device. The signal emitting device may be positioned in the mannequin 118 at a position that would occupy the simulated organ in a human body, and the signal receiving device may be located in the probe 116. Alternatively, the signal emitting device may be positioned at any position within the mannequin 118. The signal emitting device is adapted to emit a signal in multiple directions and the emitted signal varies as a function of the direction. The signal receiving device is adapted to receive the emitted signal, determine the position and orientation of the probe 116 using the received signal and the position of the signal emitting device, and send the determined position and orientation to the processor 122. Alternatively, the signal receiving device is adapted to send data representative of the received signal to the processor 122 which is adapted to determine the position and orientation of the probe 116. In another example, the position tracking system comprises a sensor adapted to measure a signal emitted or reflected by a trackable device located on the probe 116. The processor 122 is adapted to determine the position and orientation of the probe 116 as a function of data received from the sensor. The mannequin 118 can be provided with a reference marker providing a reference position for the probe 116.

Any imaging device which allows for the selection of a particular view or slice of an organ can be used. In one embodiment, the imaging device is a real imaging device used to take real medical images of an organ and provided with an adequate 3D position tracking device. For example, the imaging device can be a real probe provided with an adequate 3D position tracking device.

In another embodiment, the imaging device is shaped and sized to mimic a real imaging device that would be used to take real medical images of the organ. For example, the imaging device can be a fake probe provided with an adequate position tracking device.

In a further embodiment, the imaging device is a handheld device of which the size and/or shape is not related to that of the real imaging device that would be used to generate a real medical image of the organ. For example, the imaging device can be a mouse of the computer 112, a joystick, or the like. In this case, a virtual probe on a representation of a body may be displayed on the display unit 114. By manipulating the mouse or the joystick, the user displaces the virtual probe on the virtual body and the image 124 is displayed as a function of the position and orientation of the virtual probe on the display unit 114. Alternatively, no virtual probe is provided and only a mouse or joystick is used. Any system or device allowing the determination of the location and orientation of the imaging device may be used.

In one embodiment, the simulated ultrasound images may be animated to simulate echocardiography or obstetrical ultrasound imaging, for example. In this case, the value of density associated with each point or voxel of the 3D model, the parameter R, and/or the position of the point or voxel is time dependent. Hence, the beating of a heart may be reproduced for example. The frequency of the movement of the simulated organ can be changed during the training to be more realistic.

In one embodiment, a user of the simulator 110 may vary the power and/or frequency of the simulated ultrasounds. In order to simulate a variation of power and/or frequency, the processor 122 applies a filter to the ultrasound image 124. This results in a modified ultrasound image 124 associated with a different ultrasound frequency and/or power. Alternatively, the 3D model stored in the memory 120 may contain a different set of density values for each point and/or voxel. A set of density values corresponds to a particular ultrasound power and/or frequency.

In one embodiment, the 3D model is a realistic and accurate representation of the organ. Alternatively, the 3D model can be a simplified representation of the organ. It should be understood that any feature can be included in the 3D model.

In one embodiment, the ultrasonographic simulator 110 can also simulate Doppler images. The Doppler technology allows the determining of the speed and direction of blood flow by utilizing the Doppler Effect. In this case, the 3D model of the organ saved in memory 120 also contains information relative to the speed and direction of blood. Each point or doxel of the 3D model is associated with a value of velocity in addition to other values required to simulate ultrasound images.

In one embodiment, the ultrasound simulator 110 is adapted to generate simulated M-mode ultrasound images. An M-mode ultrasound image is an image along a single line of fire according to time (time-motion ultrasonography).

The ultrasound imaging simulator 110 can be provided with several 3D models representing different organs or different models of a same organ. For example, a user can start his training by using simplified models of an organ. As the user is getting familiar with the ultrasound scan technology, more complicated and accurate models can be used.

The mannequin 118 can be provided with an oesophagus to train a user to the technique of transesophageal echocardiography. In this case, the user inserts the probe 116 into the mannequin's oesophagus. Simulated ultrasound images of the heart are then displayed on display 114 according to the position and orientation of the probe 116.

In one embodiment, the simulator comprises 3D models of different organs so that a user can be trained on the ultrasound imaging of different organs while using a single and same simulator. In this case, the mannequin 118 is adapted to the number and type of organs stored in the computer 112. For example, the mannequin may comprise an abdomen and/or a thorax and/or a head, and/or the like.

It should be noted that the above illustrated methods and apparatus may be used to simulate two-dimensional and/or three-dimensional echography.

It should be understood that the above illustrated methods and apparatus may be used to simulate other techniques of medical imaging, such as magnetic resonance imaging, angiograms, CT scans, and the like.

It should be noted that the embodiments of the invention described above are intended to be exemplary only. The present invention can be carried out as a method, can be embodied in a system or a computer readable medium. The scope of the invention is therefore intended to be limited solely by the scope of the appended claims.

We claim:

1. A method for simulating an imaging process for an organ, said method comprising:
    retrieving from a memory a 3D volume model of said organ, said 3D volume model describing a 3D structure of said organ and a distribution of density within said 3D structure, said 3D structure representing a surface and internal features of said organ;
    generating a slice of said 3D model according to a position and an orientation of an imaging device, said slice including a cross-section of said surface and said internal features;
    generating a 3D surface model of said organ;
    distributing position points within said 3D surface model, each one of said points having a 3D spatial coordinate;
    associating a density value to each one of said position points, thereby obtaining a cloud of data points;

storing said cloud of data points in said memory as said 3D volume model;
rendering an image in accordance with said slice; and
displaying said image.

2. The method as claimed in claim 1, further comprising:
performing a voxelization of said cloud of data points; and
associating a density value with each one of said voxels as a function of said density value of said data points, thereby obtaining a grid of voxels; and
storing said grid of voxels in said memory as said 3D volume model.

3. The method as claimed in claim 1, wherein an internal surface of said 3D volume model defines a volume with no position points therein.

4. The method as claimed in claim 1, wherein said associating said density value to each one of said position points comprises associating a time-varying density value to each one of said position points.

5. The method as claimed in claim 1, wherein said rendering said image further comprises refining said image to obtain a realistic texture for said image.

6. The method as claimed in claim 1, wherein said generating a slice comprises generating a slice according to a position and an orientation of a probe, and said rendering and said displaying respectively comprise rendering an ultrasound image and displaying said ultrasound image.

7. The method as claimed in claim 1, wherein said retrieving said 3D volume model of said organ comprises retrieving a 3D volume model of a heart.

8. The method as claimed in claim 7, further comprising animating said heart.

9. A computer readable memory having recorded thereon a set of data representative of a 3D volume model of an organ and statements and instructions for execution by a processor to carry out steps of:
slicing the 3D volume model in accordance with a position and orientation of an imaging device,
generating a 3D surface model of said organ,
distributing position points within said 3D surface model, each one of said points having a 3D spatial coordinate,
associating a density value to each one of said position points, thereby obtaining a cloud of data points,
storing said cloud of data points in said computer readable memory as said 3D volume model,
rendering an image in accordance with said slice, and
displaying said image, said 3D volume model describing a 3D structure of said organ and a distribution of density within said 3D structure, said 3D structure representing a surface and internal features of said organ, said slice including a cross-section of said surface and said internal features.

10. The computer readable memory as claimed in claim 9, wherein said data set comprises voxels, wherein each voxel is associated with a volume of said voxel, a 3D spatial coordinate, and a density value.

11. The computer readable memory as claimed claim 9, wherein said density value is time-varying.

12. The computer readable memory as claimed in claim 9, further comprising a step of refining said image to obtain a realistic texture for said image.

13. A system for simulating an imaging process, comprising:
an imaging device;
a position tracking device adapted to determine a position and orientation of said imaging device; and
a machine comprising a memory having a set of data representative of a 3D volume model of an organ stored therein and a processor configured for:
slicing the 3D volume model in accordance with said position and orientation of said imaging device,
generating a 3D surface model of said organ,
distributing position points within said 3D surface model, each one of said points having a 3D spatial coordinate,
associating a density value to each one of said position points, thereby obtaining a cloud of data points,
storing said cloud of data points in said computer readable memory as said 3D volume model,
rendering an image in accordance with said slice, and
displaying said image on a display unit, said 3D volume model describing a 3D structure of said organ and a distribution of density within said 3D structure, said 3D structure representing a surface and internal features of said organ, said slice including a cross-section of said surface and said internal features.

14. The system as claimed in claim 13, wherein said data set comprises voxels, wherein each voxel is associated with a volume of said voxel, a 3D spatial coordinate, and a density value.

15. The system as claimed in claim 13, wherein said density value is time-varying.

16. The system as claimed in claim 13, wherein said processor is configured for refining said image to obtain a realistic texture for said image.

17. The system as claimed in claim 13, wherein said imaging device is a probe, said position tracking device is adapted to determine a position and orientation of said probe, and said processor is configured for rendering an ultrasound image of said organ and displaying said ultrasound image.

18. The system as claimed in claim 13, wherein said set of data is representative of a 3D model of a heart.

19. The system as claimed in claim 18, wherein said set of data is representative of a 3D model of an animated heart.

20. The method as claimed in claim 1, further comprising:
creating an animated 3D model of said organ based on said retrieved 3D volume model;
wherein, generating said slice of said 3D model comprises generating a slice of said animated 3D model, rendering said image comprises rendering an animated ultrasound image, and displaying said image comprises displaying said animated ultrasound image and said animated 3D model.

21. The method as claimed in claim 20, wherein said displaying comprises displaying any movement and/or frequency of movement of the animated 3D model.

22. The computer readable memory as claimed in claim 9, wherein:
said processor is further configured for creating an animated 3D model of said organ based on said 3D volume model;
slicing said 3D volume model comprises slicing said animated 3D model;
rendering said image comprises rendering an animated ultrasound image; and
displaying said image comprises displaying said animated ultrasound image and said animated 3D model.

23. The computer readable memory as claimed in claim 22, wherein said displaying comprises displaying any movement and/or frequency of movement of the animated 3D model.

24. The system as claimed in claim 13, wherein:
said processor is further configured for creating an animated 3D model of said organ based on said 3D volume model;
slicing said 3D volume model comprises slicing said animated 3D model;
rendering said image comprises rendering an animated ultrasound image; and
displaying said image comprises displaying said animated ultrasound image and said animated 3D model.

25. The computer readable memory as claimed in claim 24, wherein said displaying comprises displaying any movement and/or frequency of movement of the animated 3D model.

\* \* \* \* \*

UNITED STATES PATENT AND TRADEMARK OFFICE
CERTIFICATE OF CORRECTION

| | | |
|---|---|---|
| PATENT NO. | : 9,020,217 B2 | Page 1 of 1 |
| APPLICATION NO. | : 13/120936 | |
| DATED | : April 28, 2015 | |
| INVENTOR(S) | : Robert Amyot et al. | |

It is certified that error appears in the above-identified patent and that said Letters Patent is hereby corrected as shown below:

On the title page item (73), left column, Assignee "Cae Healthcare Canada Inc." should read -- CAE Healthcare Canada Inc. --

In the claims,

Claim 11, Column 11, line 58, "as claimed claim 9" should read -- as claimed in claim 9 --.

Signed and Sealed this
Twenty-fifth Day of August, 2015

Michelle K. Lee
*Director of the United States Patent and Trademark Office*